(12) United States Patent
Delmotte

(10) Patent No.: US 12,343,385 B2
(45) Date of Patent: Jul. 1, 2025

(54) HEMOSTAT RECONSTITUTION METHODS AND DEVICES

(71) Applicants: BAXTER INTERNATIONAL INC., Deerfield, IL (US); BAXTER HEALTHCARE SA, Glattpark (CH)

(72) Inventor: Yves Delmotte, Neufmaison (BE)

(73) Assignees: Baxter International Inc., Deerfield, IL (US); Baxtter Healthcare SA, Glattpark (CH)

( * ) Notice: Subject to any disclaimer, the term of this patent is extended or adjusted under 35 U.S.C. 154(b) by 431 days.

(21) Appl. No.: 17/985,427

(22) Filed: Nov. 11, 2022

(65) Prior Publication Data

US 2023/0165944 A1   Jun. 1, 2023

Related U.S. Application Data

(60) Provisional application No. 63/283,781, filed on Nov. 29, 2021.

(51) Int. Cl.
*A61K 38/48* (2006.01)
*A61L 24/00* (2006.01)

(52) U.S. Cl.
CPC ...... *A61K 38/4833* (2013.01); *A61L 24/0031* (2013.01); *A61L 2400/04* (2013.01)

(58) Field of Classification Search
CPC .............. A61K 38/4833; A61K 9/0019; A61K 38/014; A61L 24/0031; A61L 2400/04; A61L 24/043; A61L 24/10
See application file for complete search history.

(56) References Cited

U.S. PATENT DOCUMENTS

| | | | | |
|---|---|---|---|---|
| 5,364,350 | A  * | 11/1994 | Dittmann | A61K 9/0019 604/416 |
| 6,063,061 | A | 5/2000 | Wallace et al. | |
| 6,066,325 | A | 5/2000 | Wallace et al. | |
| 6,419,656 | B1 * | 7/2002 | Vetter | A61M 5/31553 604/211 |
| 6,706,690 | B2 | 3/2004 | Reich et al. | |
| 7,320,962 | B2 | 1/2008 | Reich et al. | |
| 7,435,425 | B2 | 10/2008 | Qian et al. | |

(Continued)

FOREIGN PATENT DOCUMENTS

| | | |
|---|---|---|
| EP | 2575770 | 4/2013 |
| EP | 2575775 | 4/2013 |

(Continued)

OTHER PUBLICATIONS

Written Opinion for Application No. PCT/US2022/079740 dated Oct. 13, 2023 (8 pages).

(Continued)

*Primary Examiner* — Julian W Woo
(74) *Attorney, Agent, or Firm* — K&L Gates LLP

(57) ABSTRACT

A kit and system for use in establishing local hemostasis includes a first and a second syringe. The first syringe is co-loaded with at least one substrate material and at least one hemostatic agent including a membrane separating the substrate material and the hemostatic agent. The second syringe is loaded with a diluent. In an embodiment, the kit or system includes crosslinked gelatin particles and thrombin, and the diluent is saline.

20 Claims, 12 Drawing Sheets

(56) References Cited

U.S. PATENT DOCUMENTS

| | | |
|---|---|---|
| 7,871,637 B2 | 1/2011 | Qian et al. |
| 8,092,820 B2 | 1/2012 | Qian et al. |
| 8,303,981 B2 | 11/2012 | Wallace et al. |
| 8,357,378 B2 | 1/2013 | Wallace et al. |
| 8,383,141 B2 | 2/2013 | Qian et al. |
| 8,512,729 B2 | 8/2013 | Wallace et al. |
| 8,603,511 B2 | 12/2013 | Wallace et al. |
| 8,940,335 B2 | 1/2015 | Goessl |
| 9,084,728 B2 | 7/2015 | Goessl et al. |
| 9,408,945 B2 | 8/2016 | Goessl et al. |
| 9,821,025 B2 | 11/2017 | Hedrich et al. |
| 9,833,541 B2 | 12/2017 | McCoy et al. |
| 10,245,348 B2 | 4/2019 | Goessl et al. |
| 10,322,170 B2 | 6/2019 | Gulle et al. |
| 10,994,045 B2 | 5/2021 | Goessl et al. |
| 11,583,610 B2 | 2/2023 | Scott et al. |
| 2005/0226916 A1* | 10/2005 | Cochrum ............... A61P 17/02 424/445 |
| 2008/0275387 A1* | 11/2008 | Yeadon ............... A61M 5/284 604/82 |
| 2021/0001002 A1† | 1/2021 | Park |
| 2023/0094351 A1* | 3/2023 | Addison ............... A61L 24/043 606/214 |

FOREIGN PATENT DOCUMENTS

| | | |
|---|---|---|
| EP | 2771027 | 9/2014 |
| EP | 2575775 B1 † | 4/2018 |

OTHER PUBLICATIONS

International Search Report and Written Opinion for Application No. PCT/US2022/079740 dated Mar. 27, 2023 (5 pages).
International Preliminary Report on Patentability dated Jan. 15, 2024 (6 pages).
Lewis et al., 2013, Journal of Investigative Surgery, 26, 141-148 (Lewis).†

\* cited by examiner
† cited by third party

Device 9

HEMOSTAT RECONSTITUTION METHODS AND DEVICES

CROSS-REFERENCE TO RELATED APPLICATIONS

The present application claims priority to U.S. Patent Application No. 63/283,781, filed on Nov. 29, 2021, the disclosure of which is incorporated herein by reference for all purposes.

FIELD

The present Specification relates to the preparation and use of hemostatic materials.

BACKGROUND

Control of topical bleeding is of critical importance in wound management, particularly for the management of trauma, e.g., as a result of traumatic injury or surgery. Typical methods of controlling bleeding employ the use of "passive" devices including cotton gauze pads. Passive devices, however, do not initiate or accelerate blood clotting.

In contrast to passive devices, hemostats are "active" materials that promote hemostasis through the use of hemostatic agents, for example, fibrinogen or thrombin, and actively participate in the coagulation cascade to form a fibrin clot. Thrombin is a serine protease that plays important roles in blood clotting (coagulation). As the key coagulation protease, thrombin converts soluble fibrinogen into fibrin networks crosslinked by a transglutaminase (FXIII). In addition, thrombin is the most potent activator of platelets by stimulating protease-activated receptors (PAR). Upon activation by thrombin, platelets physically alter the conformation of GP IIb/IIIa receptors and provide high-affinity binding sites for fibrinogen, providing fibrinogen-crosslinked platelet aggregation.

However, while current hemostats are effective, readying hemostats for use can require trained personnel to spend critical seconds in the preparation process. Therefore, improved methods and systems are desirable.

SUMMARY

The instant disclosure provides a novel class of delivery systems, devices, and methods which enable faster reconstitution of hemostatic materials. For example, FLOSEAL™ preparation requires that the granular gelatin substrate be reconstituted with a thrombin solution. Though not complex, this process takes time, requiring the operator to first prepare the thrombin solution, and then mix the thrombin solution with the gelatin matrix. In contrast, the instant disclosure provides systems and devices that simplify and accelerate this process. For example, disclosed embodiments combine a hemostatic agent such as thrombin with a substrate carrier material, such as gelatin granules, in a single container such as, for example, a syringe.

Disclosed systems and device also provide increased stability of hemostatic materials, for example by maintaining a moisture-free environment for the hemostatic agent.

Disclosed embodiments also comprise kits comprising the disclosed hemostatic materials, devices, and systems.

Disclosed embodiments also comprise methods of use. For example, disclosed systems, devices, and methods can be used to reduce or stop bleeding, for example bleeding associated with surgical procedures, injuries, wounds, and the like. Embodiments can comprise treatment of various categories of bleeding, including:

Grade 1: Mild
  a. For example, capsular liver abrasion. Grade 1 bleeds represent a general ooze, which well up over 1-2 minutes after blotting with gauze.

Grade 2: Moderate
  a. Grade 2 bleeds visibly well up after blotting, and are usually considered distracting to the surgical procedure.

Grade 3: Severe
  a. For example, rupture of venous plexus during posterior lumbar laminectomy. Grade 3 bleeds well up immediately after blotting, and require treatment to continue with the surgery.

Grade 4: Life Threatening
  a. For example, abdominal aortic tear. Grade 4 bleeds are life-threatening and require immediate surgical treatment.

DETAILED DESCRIPTION

Figure 1:
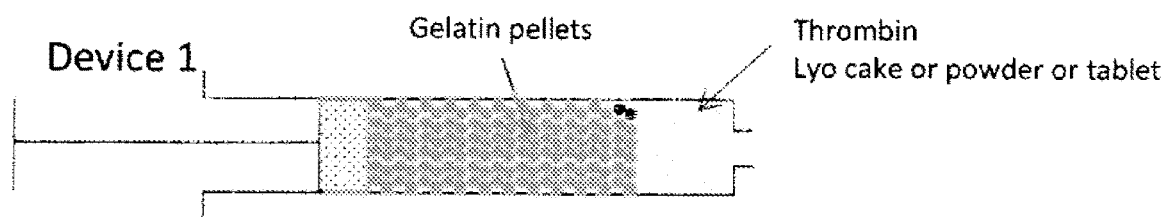
FIG. 1 shows a disclosed syringe pre-filled with thrombin and gelatin. In this embodiment, the two components are spatially separated.

Disclosed embodiments comprise a novel class of delivery systems, devices, and methods that enable faster reconstitution of hemostatic materials. Disclosed embodiments combine a hemostatic agent, for example thrombin, and a substrate material, for example gelatin particles, pellets or granules, in a single container such as a syringe. Disclosed systems can comprise at least one additional container such as a syringe comprising a diluent, for example saline or water.

Further embodiments comprise barriers or membranes physically separating the substrate material particles and the hemostatic agent inside the syringe. Disclosed membranes or barriers can prevent interaction between the components, such that the hemostatic agent is unaffected by moisture associated with the particles, such as cross-linked gelatin particles, prior to mixing the components. This physical separation can provide significant advantages, particularly when used in embodiments comprising pre-swollen substrate particles, as typical hemostatic agents can degrade over time in the presence of moisture.

In embodiments, the membrane can comprise any biocompatible, dissolvable or friable film which forms an effective moisture barrier between the hemostatic agent component such as thrombin and the substrate particles, such as cross-linked gelatin particles. Such a moisture barrier can be especially advantageous is embodiments comprising pre-swollen particles, such as cross-linked gelatin particles.

In embodiments, the membrane comprises a material with appropriate separation characteristics under mechanically (for example manually) applied liquid forces, such as via a syringe plunger, such that the membrane barrier degrades quickly upon exposure to liquid.

In embodiments, suitable membrane or barrier materials can comprise, for example a gelatin or hydrogel. Suitable hydrogels can be resorbable and comprise small subunits having a size and other physical properties which enhance the performance of the gel membrane. In particular, the subunits can be sized to permit them to flow when the hemostatic material components are subjected to stresses above a threshold level, for example when extruded through a syringe. The threshold stresses are typically in the range from $3\times10^4$ Pa to $5\times10^5$ Pa. In embodiments the membrane can remain generally immobile when subjected to stresses below the threshold level.

Disclosed embodiments can also comprise a foam. The foam provides a pre-matrix structure which is rapidly "wettable," thus forming a deliverable hemostatic paste material more quickly than dry-powder mixes or sequentially loaded syringes.

In embodiments, disclosed devices provide increased formulation stability, for example thrombin stability. For example, separately loading a hemostatic agent such as thrombin and a substrate material such as gelatin granules places the separate components in close physical proximity in a single device (thus simplifying storage and transport) while maintaining the thrombin in a dry state. In embodiments the separation is achieved spatially (without a membrane or barrier), while in some embodiments the separation is maintained through the use of the membrane or barrier.

Disclosed embodiments can further comprise a diluent, for example in a separate container such as a syringe. In embodiments, the diluent can comprise, for example, saline or water.

Disclosed embodiments can comprise means for connecting multiple syringes, such as, for example luer locks, tubing, or the like.

Definitions:

"Administration," or "to administer" means the step of giving (i.e. administering) a hemostatic device, material or agent to a subject. The materials disclosed herein can be administered via a number of appropriate routes.

"Co-loading" or "co-loaded" means multiple components are loaded into a vessel or container such as a syringe. Co-loading can encompass sequentially or simultaneously loading the multiple components. Co-loaded materials can form a mixture in a vessel, or can be separated, for example spatially, or physically by a membrane or barrier.

"Equilibrium swell" is defined as the percent swell at equilibrium after a polymeric pellet or particle material has been immersed in a wetting agent for a time period sufficient for water content to become constant, typically 18 to 24 hours. The equilibrium swell is typically determined by the amount of cross-linking within a polymeric pellet or particle.

"Hemostatic agent" means an agent that can initiate and stabilize blood clot growth during bleeding, including biologics such as thrombin, small molecules such as tranexamic acid (TXA), polymers such as feracrylum, peptides such as Thrombin Receptor Activating Peptides (TRAPs), polysulfonic acid polymers, sulfated icodextrin, sulfated carbohydrates, and inorganic materials such as kaolin.

"Hemostatic material" means a material comprising a hemostatic agent in a form suitable for application to a patient.

"Patient" means a human or non-human subject receiving medical or veterinary care.

"Therapeutically effective amount" means the level, amount or concentration of an agent, material, or composition needed to achieve a treatment goal.

"Treat," "treating," or "treatment" means an alleviation or a reduction (which includes some reduction, a significant reduction, a near total reduction, and a total reduction), resolution or prevention (temporarily or permanently) of a symptom, disease, disorder or condition, so as to achieve a desired therapeutic or cosmetic result, such as by healing of injured or damaged tissue, or by altering, changing, enhancing, improving, ameliorating and/or beautifying an existing or perceived disease, disorder or condition.

The instant disclosure provides systems and devices for hemostatic material storage and administration, said hemostatic materials comprising at least one hemostatic agent and at least one substrate carrier.

Hemostatic Materials

Disclosed hemostatic materials comprise at least one hemostatic agent and at least one particle substrate material.

Hemostatic Agents

Disclosed hemostatic materials comprise at least hemostatic agents comprising, for example, thrombin, small molecules such as tranexamic acid (TXA), feracrylum, peptides such as Thrombin Receptor Activating Peptides (TRAPs), polysulfonic acid polymers, sulfated icodextrin, sulfated carbohydrates, analogs thereof, and inorganic materials such as kaolin. In embodiments, the hemostatic agent can be of native or recombinant origin. In embodiments, multiple hemostatic agents can be employed.

Particle Substrates

Disclosed hemostatic materials comprise carrier substrates such as particles, pellets, or granules, for example granules comprising cross-linked materials comprising at least one biologic or non-biologic polymer, for example proteins, polysaccharides, and synthetic polymers.

In embodiments the substrate polymer is biodegradable. Biodegradable polymers release contained drugs as the matrix is consumed or biodegraded during therapy. The polymer is usually selected to breakdown into subunits which are biocompatible with the surrounding tissue. The persistence of a biodegradable polymer in vivo depends on its molecular weight and degree of cross-linking, the higher the molecular weights and degrees of cross-linking resulting in a longer life. Common biodegradable polymers include polylactic acid (PLA, also referred to as polylactide), polyglycolic acid (PGA), copolymers of PLA and PGA, polyamides, and copolymers of polyamides and polyesters.

In various embodiments, the substrate material comprises a recombinant polymer. In particular, the recombinant polymer can be a recombinant human collagen, such as, for example, recombinant human collagen type I, recombinant human collagen type III, or a combination thereof. In one embodiment, the substrate material comprises recombinant human collagen type III. In another embodiment, the substrate material comprises recombinant human collagen type I. For example, the recombinant human gelatin can be derived from recombinant human collagen type III. In yet another embodiment, the substrate material comprises recombinant gelatin derived from recombinant human collagen type I. In further embodiments, the substrate material comprises recombinant gelatin produced directly by expression of encoding polynucleotide. In embodiments, collagen can be derived from animal tissues such as bovine, porcine, or equine tissue, or from human sources.

The polysaccharide used as a biocompatible substrate material in disclosed embodiments can comprise, for example, cellulose, alkyl cellulose, methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparan, heparan sulfate, dermatan sulfate, keratan sulfate, carrageenans, chitosan, starch, amylose, amylopectin, poly-N-glucosamine, polymannuronic acid, polyglucuronic acid, polyguluronic acid, derivatives of said polysaccharides, or combinations thereof.

The present biocompatible substrate material can also be based on a synthetic polymer. The synthetic absorbable polymer can be an aliphatic polyester polymer, an aliphatic polyester copolymer, or combinations thereof.

In embodiments, the polymer is capable of being cross-linked and hydrated to form a hydrogel. Exemplary polymers include proteins selected from gelatin, collagen (e.g. soluble collagen), albumin, fibrinogen, fibrin, fibronectin, elastin, keratin, laminin, casein and derivatives and combinations thereof. Alternatively, the polymer may comprise a polysaccharide, such as a glycosaminoglycan (e.g., hyaluronic acid or chondroitin sulfate), a starch derivative, a cellulose derivative, a hemicellulose derivative, xylan, agarose, alginate, chitosan, and combinations thereof. As a further alternative, the polymer may comprise a non-biologic hydrogel-forming polymer, such as polyacrylates, polymethacrylates, polyacrylamides, polyvinyl polymers, polylactide-glycolides, polycaprolactones, polyoxyethylenes, and derivatives and combinations thereof.

Cross-linking of the polymer may be achieved in any conventional manner. For example, in the case of proteins, cross-linking may be achieved using a suitable cross-linking agent, such as an aldehyde, sodium periodate, epoxy compounds, and the like. Alternatively, cross-linking may be induced by exposure to radiation, such as γ-radiation or electron beam radiation. Polysaccharides and non-biologic polymers may also be cross-linked using suitable cross-linking agents and radiation. Additionally, non-biologic polymers may be synthesized as cross-linked polymers and copolymers. For example, reactions between mono- and poly-unsaturated monomers can result in synthetic polymers having controlled degrees of cross-linking. Typically, the polymer molecules will each have a molecular weight in the range from 20 kD to 200 kD, and will have at least one link to another polymer molecule in the network, often having from 1 to 5 links, where the actual level of cross-linking is selected in part to provide a desired rate of biodegradability and "swell" in the ranges set forth below. Exemplary methods for producing molecular cross-linked gelatins are as follows.

Gelatin is obtained and placed in an aqueous buffer to form a non-cross-linked hydrogel, typically having a solids content from 1% to 70% w/w, usually from 3% to 10% by weight. The gelatin is then cross-linked, typically by exposure to either glutaraldehyde (e.g. 0.01% to 0.05% w/w, overnight at 0° C. to 15° C. in aqueous buffer), sodium periodate (e.g. 0.05 M, held at 0° C. to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation.

Alternatively, gelatin particles can be suspended in an alcohol, preferably methyl alcohol or ethyl alcohol, at a solids content of 1% to 70% by w/w, usually 3% to 10% by weight, and cross-linked by exposure to a cross-linking agent, typically glutaraldehyde (e.g., 0.01% to 0.1% w/w, overnight at room temperature). In the case of aldehydes, the pH should be held from about 6 to 11, preferably from 7 to 10. When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol, dried and resuspended to a desired degree of hydration in an aqueous medium having a desired buffer and pH. The resulting hydrogels may then be loaded into the applicators of the present disclosure. Alternatively, the hydrogels may be mechanically disrupted prior to or after cross-linking. In embodiments, genipin can be employed as a cross-linker.

The extent of cross-linking of the polymer has an effect on several functional properties of the hydrogel including extrudability, adsorptiveness of surrounding biological fluids, cohesiveness, ability to fill space, swelling ability and ability to adhere to the tissue site. The extent of cross-linking of the polymeric hydrogel composition may be controlled by adjusting the concentration of cross-linking agent, controlling exposure to cross-linking radiation, changing the relative amounts of mono- and poly-unsaturated monomers, varying reaction conditions, and the like. Typically, the degree of cross-linking is controlled by adjusting the concentration of cross-linking agent.

Disclosed hydrogels of the instant disclosure will typically have a solids content in the range from 1% by weight to 70% w/w. Optionally, the compositions may comprise at least one plasticizer as described in more detail below. Suitable plasticizers include polyethylene glycols, sorbitol, glycerol, and the like.

The equilibrium swell of the cross-linked polymers of the present disclosure may range from 400% to 5000%, 400% to 3000%, 400% to 2000%, usually ranging from 400% to 1300%, preferably being from 500% to 1100%, depending on its intended use. Such equilibrium swell may be controlled by varying the degree of cross-linking, which in turn is achieved by varying the cross-linking conditions, such as the type of cross-linking method, duration of exposure of a cross-linking agent, concentration of a cross-linking agent, cross-linking temperature, and the like.

Exposure to radiation, such as γ-radiation, may also be carried out in order to sterilize the components before or after packaging. When the compositions are composed of radiation-sensitive materials, it will be necessary to protect the compositions from the undesirable effects of sterilizing radiation. For example, in some cases, it will be desirable to add a stabilizer, such as ascorbic acid, in order to inhibit degradation and/or further excessive cross-linking of the materials by free radical mechanisms.

In embodiments, x-ray, e-beam, and beta sterilization can be used.

Systems and Devices

Disclosed embodiments comprise systems and devices comprising vessels, for example syringes. Disclosed systems can comprise at least one syringe comprising at least one hemostatic agent and at least one substrate comprising particles, pellets, or granules. For example, in embodiments, the hemostatic agent can comprise thrombin, fibrinogen, clotting factors, and the like.

In embodiments, the particles, pellets, or granules can comprise a material comprising hemostatic properties.

In embodiments, the hemostatic agent and the carrier substrate are co-loaded into a vessel, for example, a syringe. For example, in embodiments, the hemostatic agent and the carrier substrate are loaded sequentially into the syringe, or loaded simultaneously into the syringe. In embodiments, the substrate component can be "pre-swollen" by exposure to a liquid prior to loading the component. In embodiments, components can be frozen prior to loading the component. In embodiments, disclosed syringes can comprise a luer lock, tubing, and the like.

Turning to the embodiment of FIG. 1, the system comprises a device comprising a first layer comprising gelatin particles, pellets, or granules and a second layer comprising a hemostatic agent such as thrombin. The first layer comprises pellets having spherical or irregular shapes. The thrombin layer can comprise freeze-dried thrombin, powdered thrombin, or a thrombin tablet. In this embodiment, the two layers are not separated by a membrane. The device can be loaded either through a connector at the tip of the syringe body, or through the large opening of the syringe body prior to insertion of the piston and plunger. A cap over the connector at the tip of the syringe body prevents moisture from the interior of the device.

Figure 2:
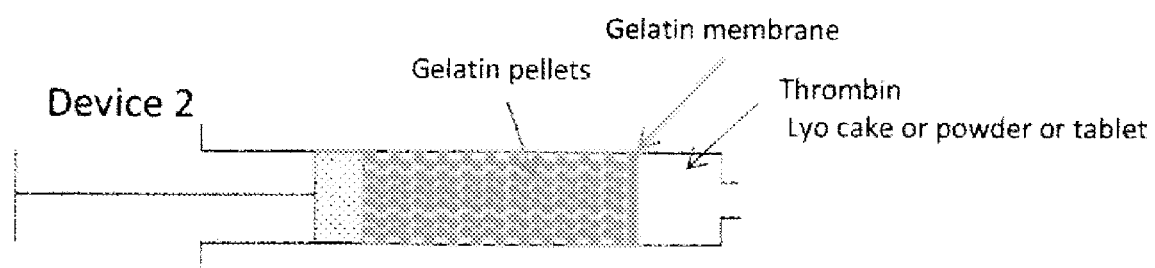
FIG. 2 shows a disclosed syringe pre-filled with thrombin and gelatin, with the two components physically separated by a gelatin membrane.

Turning to the embodiment of FIG. 2, the system comprises a device comprising a first layer comprising pellets or particles, for example gelatin pellets or particles, a membrane, for example a gelatin or hydrogel membrane, and a second layer comprising a hemostatic agent such as thrombin. In embodiments, the pellets or particles comprise spherical or irregular shapes.

The hemostatic agent (such as thrombin) layer can comprise, for example, freeze-dried thrombin, powdered thrombin, or a thrombin tablet.

In this embodiment, the two layers are physically separated by a membrane, for example a friable, fragmentable, or dissolvable membrane comprised of, for example, gelatin. The membrane maintains physical separation of the two layers until a diluent is applied and the components mixed. In embodiments, the membrane separating the two layers provides an increase in formulation stability. For example, the membrane separating the hemostatic agent from the particles or pellets can protect the hemostatic agent from moisture migration from the particle or pellet phase. The membrane can also prevent interaction of the hemostatic agent with the syringe stopper; typical stopper materials can contain oils or treatments which may inactivate the hemostatic agent during prolonged storage.

The device can be loaded through the large opening of the syringe body prior to insertion of the piston and plunger. A cap over the connector at the tip of the syringe body prevents moisture from entering the interior of the device.

Figure 3:
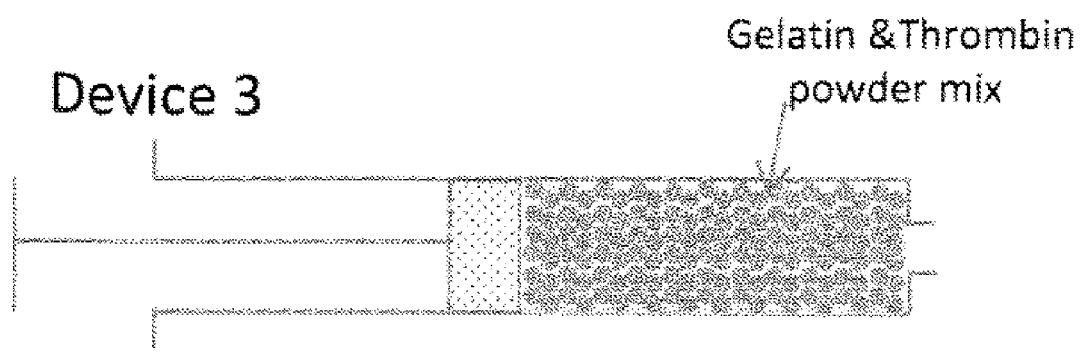
FIG. 3 shows a disclosed syringe pre-filled with a mixture of thrombin and gelatin.

Turning to the embodiment of FIG. 3, the system comprises a device comprising gelatin pellets mixed with, or coated with, or adsorbed to, thrombin. A cap over the connector at the tip of the syringe body prevents moisture from the interior of the device. In embodiments comprising gelatin pellets coated with thrombin, the coating can ensure homogenous distribution of gelatin and thrombin within the syringe.

Figure 4:
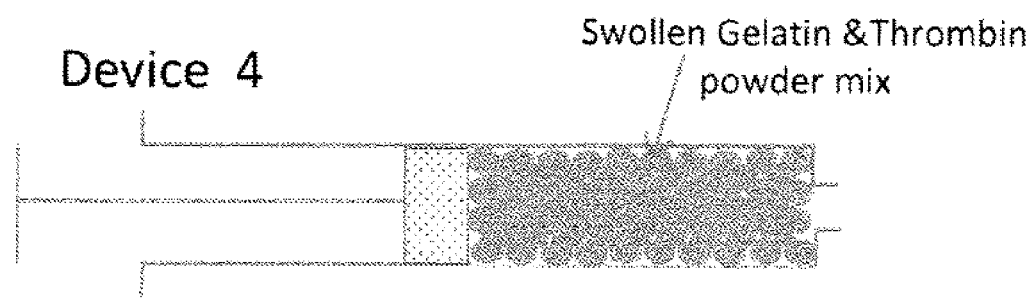
FIG. 4 shows a disclosed syringe pre-filled with a mixture of thrombin powder and swollen gelatin particles.

Turning to the embodiment of FIG. 4, the system comprises a device comprising hydrated particles or pellets, for example of gelatin, and a hemostatic agent (such as thrombin) mixture. The mixture can be swollen or un-swollen, for example by exposure to a liquid, prior to loading. For example, in embodiments, pre-swollen, cross-linked gelatin particles, pellets, or granules enable faster reconstitution and paste formation due to the particles' increased porosity, as well as providing more efficient liquid flow paths around the particles, thus accelerating dissolution of the thrombin and increasing its distribution in the hemostat matrix. The swollen particles also provide increased particle surface area for faster thrombin association with the particle, further accelerating the reconstitution process.

A cap over the connector at the tip of the syringe body prevents moisture from the interior of the device. The device can be frozen for storage, then thawed for use. Disclosed embodiments comprising per-swollen particles and the hemostatic agent can be especially suited for planned future use, such as for example within 4, 6, 8, 10, or 12 hours of thawing, such as for use in a day's planned surgeries, or in the event of a mass-casualty scenario. For example, upon notification of an incident that could potentially result in mass casualties, multiple frozen embodiments can be thawed in preparation for later use. Pre-swelling the particles or pellets also reduces the volume of diluent needed for proper reconstitution.

In embodiments, the degree of pre-swelling can be determined based upon the desired use. For example, materials having differing equilibrium swell values perform differently in different applications; inhibition of bleeding in certain applications can be most readily achieved with cross-linked gelatin materials having a swell in the range from 700% to 950%. For other applications, lower equilibrium swell values in the range from 500% to 600% can be more successful. Thus, the ability to control cross-linking and equilibrium swell allows the disclosed hemostatic materials to be optimized for a variety of uses.

Figure 5:
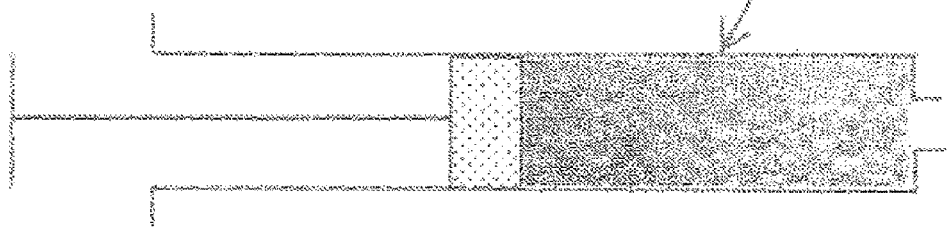
FIG. 5 shows a disclosed syringe pre-filled with a foam of thrombin and swollen gelatin particles.

Turning to the embodiment of FIG. 5, the system comprises a device comprising a foam of swollen cross-linked gelatin and a hemostatic agent such as thrombin. In embodiments, the foam can comprise a wet foam containing a liquid such as water or saline, or dried into a sponge for subsequent rehydration. The device can be loaded through the large opening of the syringe body prior to insertion of the piston and plunger. A cap over the connector at the tip of the syringe body prevents moisture from the interior of the device. In embodiments, the device can be frozen for storage. In use, the foam can be applied as a spray, for example to treat a broad area.

Figure 6:
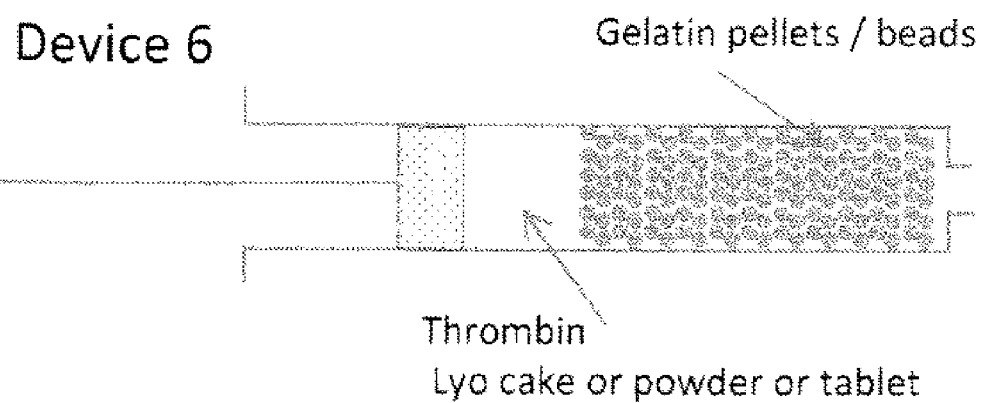
FIG. 6 shows a disclosed syringe pre-filled with thrombin and gelatin. In this embodiment, the two components are spatially separated.

Turning to the embodiment of FIG. 6, the system comprises a device comprising a first layer of, for example, gelatin particles or pellets and a second layer of freeze-dried or frozen hemostatic agent such as thrombin. The first layer comprises pellets having spherical or irregular shapes. The two layers are not physically separated with a membrane or barrier. The device can be loaded either through a connector at the tip of the syringe body, or through the large opening of the syringe body prior to insertion of the piston and plunger. A cap over the connector at the tip of the syringe body prevents moisture from the interior of the device.

Figure 7:
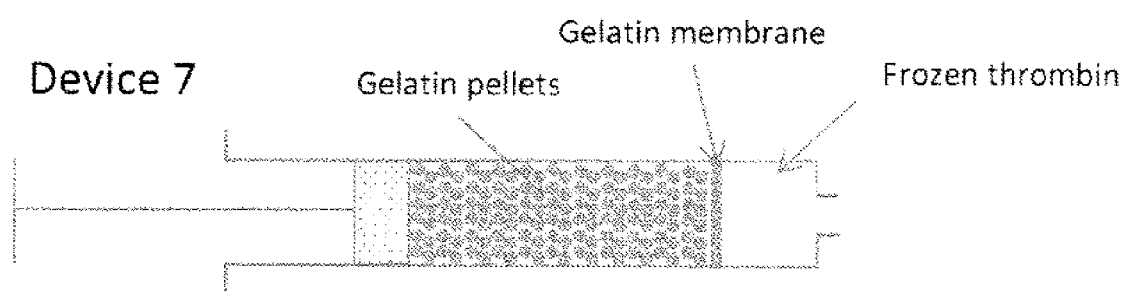
FIG. 7 shows a disclosed syringe pre-filled with thrombin and gelatin. The components are physically separated by a gelatin membrane.

Turning to the embodiment of FIG. 7, the system comprises a device comprising a first layer of gelatin particles or pellets and a second layer of frozen hemostatic agent such as thrombin. The first layer comprises pellets having spherical or irregular shapes. The two layers are separated with a membrane, for example a gelatin membrane. The device can be loaded through the large opening of the syringe body prior to insertion of the piston and plunger. In embodiments, the hemostatic agent layer is frozen inside a syringe, then the substrate particles or pellets are added, then the device is re-frozen.

A cap over the connector at the tip of the syringe body prevents moisture from the interior of the device.

Figure 8:
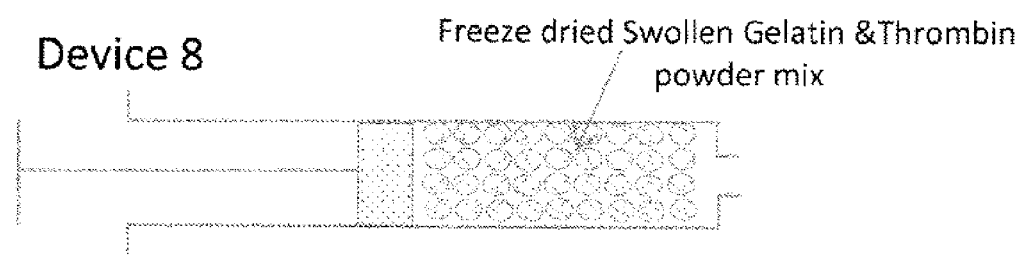
FIG. 8 shows a disclosed syringe pre-filled with a mix of thrombin and swollen gelatin particles.

Turning to the embodiment of FIG. 8, the system comprises a device comprising a foam of swollen gelatin and thrombin that has been mixed, then freeze-dried. The foam provides a pre-matrix structure which is rapidly "wettable," thus forming a deliverable hemostatic paste material more quickly than dry-powder mixes or sequentially loaded syringes. A cap over the connector at the tip of the syringe body prevents moisture from the interior of the device.

Figure 11:
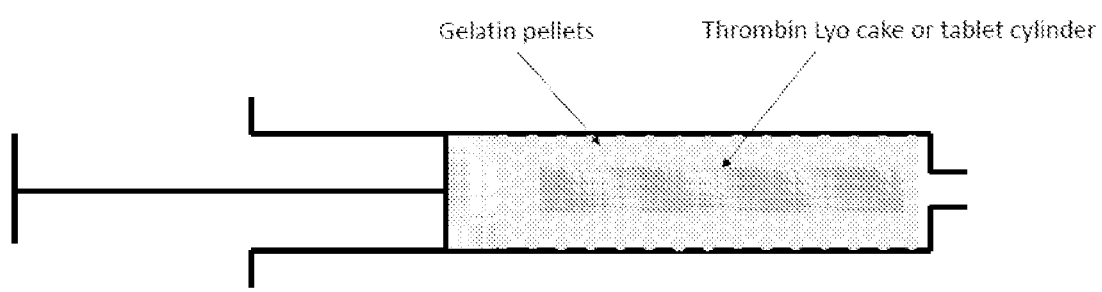
FIG. 11 shows a disclosed syringe pre-filled with a thrombin tablet or freeze dried thrombin, surrounded by gelatin pellets.

Turning to the embodiment of FIG. 11, the system comprises a device comprising a hemostatic agent (such as thrombin) tablet or cylinder, surrounded by gelatin pellets or granules. The thrombin can comprise freeze-dried thrombin. The hemostatic agent cylinder presents an increased surface area to the diluent, thus accelerating the reconstitution process.

The device can be loaded through the large opening of the syringe body prior to insertion of the piston and plunger. A cap over the connector at the tip of the syringe body prevents moisture from the interior of the device. Use of the separate thrombin tablet or cylinder can enable the use of simpler manufacturing processes.

Figure 12:
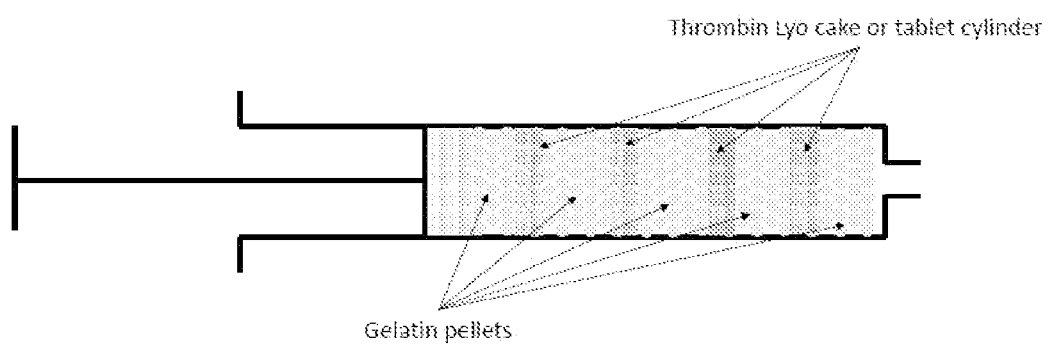
FIG. 12 shows a disclosed syringe pre-filled with a first layer of gelatin pellets and a second layer of freeze-dried or frozen thrombin, with subsequent alternating layers of gelatin and thrombin.

Turning to the embodiment of FIG. 12, the system comprises a device comprising a first layer of pellets or particles (such as gelatin pellets or particles) and a second layer of freeze-dried or frozen hemostatic agent (such as thrombin) with subsequent alternating layers of gelatin and thrombin. The gelatin layers comprise pellets having spherical or irregular shapes. The two layers are not separated with a membrane. The device can be loaded either through a connector at the tip of the syringe body, or through the large opening of the syringe body prior to insertion of the piston and plunger. A cap over the connector at the tip of the syringe body prevents moisture from the interior of the device. Use of multiple, separate thrombin tablets can enable the use of simpler manufacturing processes. Further, thinner layers of thrombin can provide for more rapid dissolution of the thrombin, as well as easier mixing of the formulation.

Commercial Products/Kits

The present hemostatic materials can be finished as a commercial product by the usual steps performed in the present field, for example by appropriate sterilization and packaging steps. The hemostatic materials according to the present disclosure can be finally sterile-wrapped so as to retain sterility until use and packaged (e.g. by the addition of specific product information leaflets) into suitable containers (boxes, etc.).

According to further embodiments, the hemostatic materials can also be provided in kit form combined with other components necessary for administration of the material to the patient. Buffer components such as phosphate, carbonate, TRIS, etc., divalent metal ions, preferably $Ca^{2+}$ ions, or other functional components (if not already present on or in the substrate), such as anti-bacterial agents, immunosuppressive agents, anti-inflammatory agents, anti-fibrinolytic agents, such as aprotinin or ECEA, growth factors, vitamins, cells, etc. The kit may further contain means for administering or preparing administering the hemostatic material, such as syringes, tubes, catheters, forceps, scissors, sterilizing pads or lotions, etc.

Disclosed kits, such as for use in surgery and/or in the treatment of injuries and/or wounds, can comprise a disclosed hemostatic material and at least one administration device, for example a buffer, a syringe, a tube, a catheter, forceps, scissors, gauze, a sterilizing pad or lotion.

In embodiments, the buffer solution further comprises an anti-bacterial agent, immunosuppressive agent, anti-inflammatory agent, anti-fibrinolytic agent, especially aprotinin or ECEA, growth factor, vitamin, cell, or mixtures thereof. Alternatively, the kit can also further comprise an anti-bacterial agent, immunosuppressive agent, anti-inflammatory agent, anti-fibrinolytic agent, especially aprotinin or ECEA, growth factor, vitamin, cell, or mixtures thereof.

Figure 9:
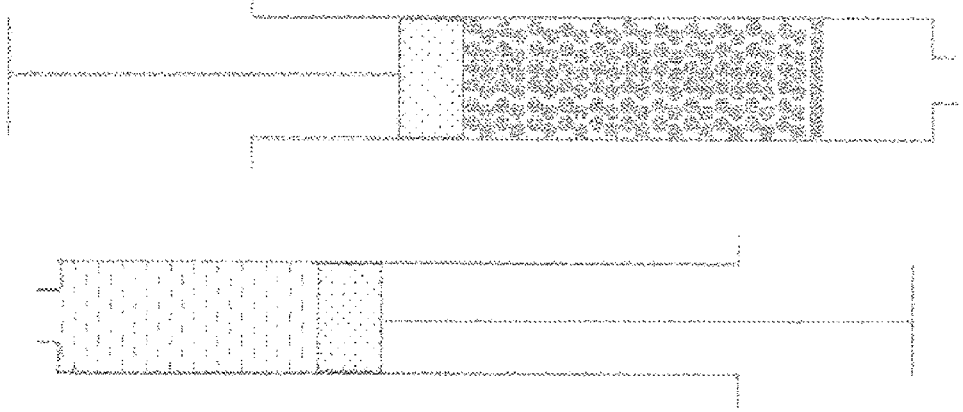
FIG. 9 shows a disclosed kit embodiment with application device, diluent syringe, and applicator.
Figure 9:
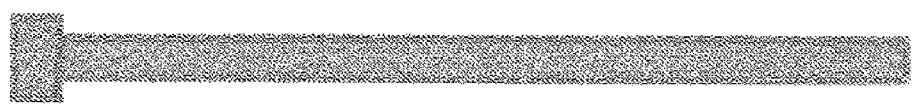

The kits are designed in various forms based on the specific deficiencies they are designed to treat. For example, FIG. 9 shows an exemplary kit comprising a double thermoformed blister containing the application device, a diluent syringe, and an applicator. Additional components, for example cannula or desiccating materials can be added.

Methods of Use

Figure 10:
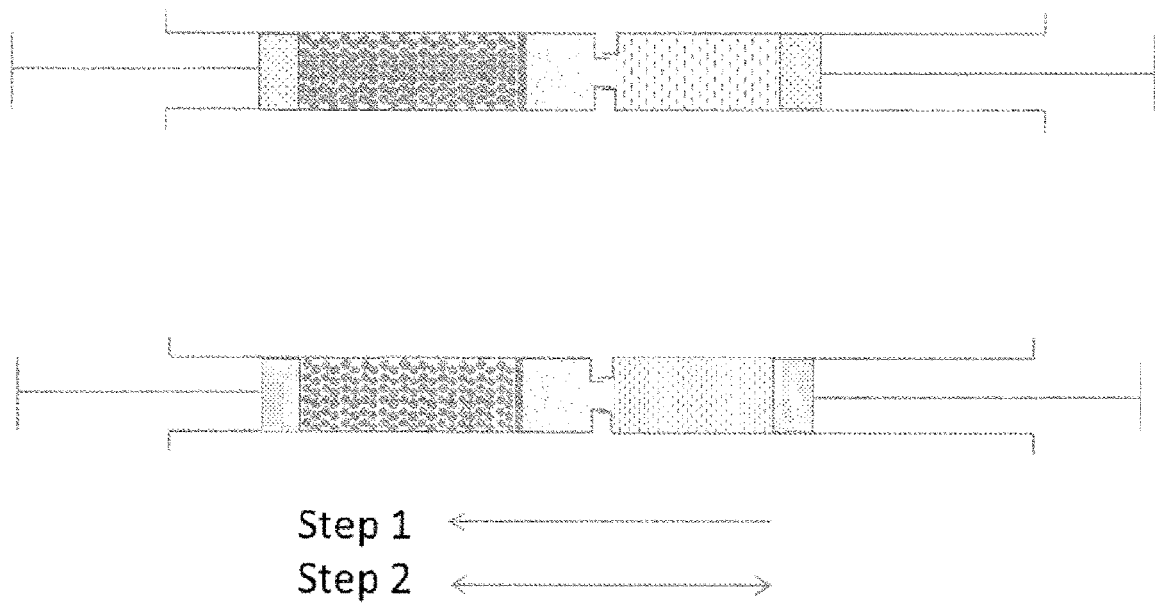
FIG. 10 shows a disclosed method of reconstituting a disclosed hemostatic material comprising gelatin granules and thrombin.

Methods of use of disclosed embodiments can comprise reconstituting the substrate, for example the cross-linked gelatin granules, with a solution containing a hemostatic agent, for example thrombin, followed by application to a site where bleeding is desired to be reduced. For example, FIG. 10 shows an exemplary method of reconstituting the hemostatic material wherein the diluent syringe is connected to the substrate/hemostatic agent syringe and the contents are "swooshed" from one syringe to the other repeatedly.

Disclosed methods of use comprise application of disclosed embodiments to a site where bleeding is desired to be reduced, such as a site of injury or surgical procedure. These methods are further described in the following Examples.

EXAMPLES

The following non-limiting Examples are provided for illustrative purposes only in order to facilitate a more complete understanding of representative embodiments. This example should not be construed to limit any of the embodiments described in the present specification.

Example 1

Production of Co-loaded Syringe

A first syringe is filled with a diluent of 0.9% NaCl.

A second syringe is first loaded through the large opening with dry cross-linked gelatin granules. Next, the second syringe is loaded through the large opening with freeze-dried thrombin.

Example 2

Production of Co-loaded Syringe

A first syringe is filled with a diluent of water.

A second syringe is simultaneously loaded through the large opening with dry cross-linked gelatin granules and freeze-dried thrombin.

Example 3

Preparation of Hemostatic Material

A first syringe containing a diluent of 0.9% NaCl (w/v) is "docked" to a second syringe containing a layer of pre-swollen cross-linked gelatin granules and a layer of freeze-dried thrombin. The two components are separate by a gelatin membrane. The diluent is injected from the first syringe into the second syringe, then the contents of the second syringe is injected back into the first syringe. This is repeated several times to hydrate the gelatin granules and reconstitute the thrombin.

The hemostatic material is then ready for use.

Example 4

Treatment of Injury

An automobile accident victim sustains traumatic injuries to the abdomen. To stop blood loss, a disclosed hemostatic material is applied to the injury site using a disclosed hemostatic material delivery device. Blood loss is reduced within minutes.

Example 5

Treatment of Surgical Incision

To stop blood loss, a disclosed hemostatic material is applied to the site of a surgical incision using a disclosed hemostatic material delivery device. Blood loss is reduced within minutes, the hemostatic material also provides an antimicrobial effect.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A system for administering a hemostatic material to a patient, the system comprising;
    a first syringe co-loaded with at least one substrate material and at least one hemostatic agent including a membrane separating said substrate material and said hemostatic agent; and
    a second syringe loaded with a diluent.

2. The system of claim 1, wherein said at least one substrate material comprises a gelatin.

3. The system of claim 2, wherein said gelatin comprises a cross-linked gelatin.

4. The system of claim 3, wherein said cross-linked gelatin comprises gelatin granules.

5. The system of claim 1, wherein said at least one hemostatic agent comprises thrombin.

6. The system of claim 1, wherein said diluent comprises sterile water.

7. The system of claim 1, wherein said diluent comprises saline.

8. The system of claim 7, wherein said saline comprises 0.9% (w/v) NaCl.

9. The system of claim 1, wherein said substrate material is pre-swollen.

10. The system of claim 1, wherein said membrane comprises a dissolvable, fragmentable, or friable material.

11. The system of claim 10, wherein said dissolvable, fragmentable, or friable material comprises a gelatin.

12. A kit for use in establishing local hemostasis, comprising;
    a first syringe co-loaded with at least one substrate material and at least one hemostatic agent including a membrane separating said substrate material and said hemostatic agent; and
    a second syringe loaded with a diluent.

13. The kit of claim 12, wherein said at least one substrate material comprises a gelatin.

14. The kit of claim 13, wherein said gelatin comprises a cross-linked gelatin.

15. The kit of claim 14, wherein said cross-linked gelatin comprises gelatin granules.

16. The kit of claim 12, wherein said at least one hemostatic agent comprises thrombin.

17. The kit of claim 12, wherein said diluent comprises sterile water.

18. The kit of claim 12, wherein said diluent comprises saline.

19. The kit of claim 18, wherein said saline comprises 0.9% (w/v) NaCl.

20. The kit of claim 12, wherein said substrate material is pre-swollen.

* * * * *